(12) United States Patent
Kiefer

(10) Patent No.: US 6,906,029 B2
(45) Date of Patent: Jun. 14, 2005

(54) INSULIN-LIKE GROWTH FACTOR BINDING PROTEIN (IGFBP-5)

(75) Inventor: Michael C. Kiefer, Clayton, CA (US)

(73) Assignee: Chiron Corporation, Emeryville, CA (US)

( * ) Notice: Subject to any disclaimer, the term of this patent is extended or adjusted under 35 U.S.C. 154(b) by 301 days.

(21) Appl. No.: 10/300,498

(22) Filed: Nov. 19, 2002

(65) Prior Publication Data

US 2003/0082744 A1 May 1, 2003

Related U.S. Application Data

(60) Division of application No. 08/345,864, filed on Nov. 28, 1994, now Pat. No. 6,500,635, which is a continuation of application No. 08/142,848, filed on Oct. 26, 1993, now abandoned, and a continuation of application No. 07/638,628, filed on Jan. 8, 1991, now abandoned.

(51) Int. Cl.[7] .............................................. C01K 14/00
(52) U.S. Cl. .............................. 514/3; 512/2; 530/399; 530/303; 530/350
(58) Field of Search ........................ 514/3, 2; 530/350, 530/303, 399

(56) References Cited

FOREIGN PATENT DOCUMENTS

| EP | 0 369 943 A1 | 5/1990 |
|---|---|---|
| WO | WO 89/08667 A1 | 9/1989 |
| WO | WO 89/09268 A1 | 10/1989 |
| WO | WO 89/09792 A1 | 10/1989 |
| WO | WO 90/00569 A1 | 1/1990 |
| WO | WO 92/14834 A1 | 9/1992 |
| WO | WO 92/18154 A1 | 10/1992 |

OTHER PUBLICATIONS

Andress et al., "A novel human insulin–like growth factor binding protein secreted by osteoblast–like cells," *Biochemical and Biophysical Research Communications* 276(1):213–218, 1991.

Andress et al., "Human osteoblast–derived insulin–like growth factor (IGF) binding protein–5–stimulates osteoblast mitogenesis and potentiates IGF action," *The Journal of Biological Chemistry* 267(31):22467–22472, 1992.

Bathurst et al., "Yeast KEX2 protease has the properties of human proalbumin converting enzyme," *Science* 235:348–350, 1987.

Baxter et al., *Bioch. Biophys. Res. Com.* 139:1256–1261, 1986.

Binkert et al., *The EMBo Journal* 8:2497–2502, 1989.

Brinkman et al., *The EMBO Journal* 7:2417–2423, 1988.

Brewer et al., *Bioch. Biophys. Res. Com.* 152:1289–1297, 1988.

Fuller et al., "The Saccharomyces Cerevisiae KEX2 Gene . . . ," *Microbiol.* 1986:273, 1986.

Fuller et al., "Intracellular targeting and structural conservation of a prohormone–processing endoprotease," *Science* 246:482, 1989.

Fuller et al., "Yeast prohormone processing enzyme . . . , " *Proc. Natl. Acad. Sci. USA* 86:1434, 1989.

Julius et al., "Glycosylation and processing of prepro–x–factor through the yeast secretory pathway," *Cell* 36:309, 1984.

Keifer et al., *Biochem. Biophys. Res. Commun.* 176(11):219, 1991.

Koistinen et al., *Endocringology* 118:1375–1378, 1986.

Lee et al., *Mol. Endocrinol.* 2:404–411, 1988.

Lyons et al., *Mol. Cell. Endocrinol.* 45:263–270, 1986.

Mohan et al., *Proc. Natl. Acad. Sci.* 86:8338–8342, 1989.

Mottola et al., *Journal of Biol. Chem.* 261:11180–11188, 1986.

Povoa et al., *Eur. J. Biochem.* 144:199–204, 1984.

Powell et al., *Chromatogr.* 420:163–170, 1987.

Roebroek, "Evolutionary conserved close linkage of the c–fes/fps proto–oncogene and genetic sequences encoding a receptor–like protein," *EMBO J.* 5:2197, 1986.

Roebroek et al., "Characterization of human c–fes/fps reveals a new transcription unit (FUR) . . . ," *Molec. Biol. Rep.* 11:117, 1986.

Shimasaki et al., 2nd International Symposium on Insulin–Like Growth Factors/Somatomedins Entitled Isolation and Molecular Characterization of Three Novel IGFBPs.

Shimasaki et al., *Mol. Endocrinology* 4:1451–1458, 1990.

Shimasaki et al., Second International IGF Symposium Abstract, 1991.

Shimasaki et al., *J. Biol. Chem.* 266(16):10646, 1991.

Shimasaki et al., "Isolation and Molecular Cloning of Insulin–like Growth Factor–Binding Protein–6," *Mol. Endocrin.* 5:938–948, 1991.

(Continued)

Primary Examiner—Karen Cochrane Carlson
(74) Attorney, Agent, or Firm—Roberta L. Robins; T. Helen Payne; Alisa A. Harbin

(57) ABSTRACT

A purified insulin-like growth factor binding protein (IGFBP) selected from the group consisting of insulin-like growth factor binding protein having an amino acid sequence that, preferably, is at least 70% homologous to the amino acid sequence of FIG. 1 and fragments thereof that are capable of binding to an antibody specific for the protein or to an insulin-like growth factor is described. This new IGFBP is designated herein as IGFBP-6. Recombinant DNA molecules encoding the binding proteins and subsequences thereof are also described along with recombinant microorganisms and cell lines containing the DNA molecules and methods for producing the binding proteins using recombinant hosts containing the relevant DNA molecules. Antibodies to the protein, useful in various diagnostic applications, are also described.

19 Claims, 1 Drawing Sheet

OTHER PUBLICATIONS

Shimasaki et al., "Identification of five different insulin–like growth factor binding proteins (IGFBPs) from adult rat serum and molecular cloning of a novel IGFBP–5 in rat and human," *Journal of Biological Chemistry* 266(16):10646–10653, 1991.

Smeekens et al., "Identification of a human insulinoma cDNA encoding a novel mammalian protein . . . ," *J. Biol. Chem.* 265:2997, 1990.

Thomas et al., "Yeast KEX2 endopeptidase correctly cleaves a neuroendocrine prohormone in mammalian cells," *Science* 241:226, 1988.

Van Den Ouweland et al., "Structural homology between the human fur gene product and the subtilisin–like protease encoded by yeast KEX2," *Nuc. Acids Res.* 18:644, 1990.

Wood et al., *Mol. Endocrinol.* 2:1176–1185, 1988.

Zapf et al., *J. Biol. Chem.* 265:14892–14898, 1990.

```
   1                                   CTCTCCTGCCCCACCCCGAGGT...AGGGGGCGACTAAGAGAAG
                                                                          ↓a
   1 Met Val Leu Leu Thr Ala Val Leu Leu Leu Leu Ala Ala Tyr Ala Gly Pro Ala
  44 ATG GTG TTG CTC ACC GCG GTC CTC CTG CTG CTG GCC GCC TAT GCG GGG CCG GCC

19 Gln Ser Leu Gly Ser Phe Val His Cys Glu Pro Cys Asp Glu Lys Ala Leu Ser
      ↓b
  98 CAG AGC CTG GGC TCC TTC GTG CAC TGC GAG CCC TGC GAC GAG AAA GCC CTC TCC

37 Met Cys Pro Pro Ser Pro Leu Gly Cys Glu Leu Val Lys Glu Pro Gly Cys Gly
 152 ATG TGC CCC CCC AGC CCC CTG GGC TGC GAG CTG GTC AAG GAG CCG GGC TGC GGC

55 Cys Cys Met Thr Cys Ala Leu Ala Glu Gly Gln Ser Cys Gly Val Tyr Thr Glu
 206 TGC TGC ATG ACC TGC GCC CTG GCC GAG GGG CAG TCG TGC GGC GTC TAC ACC GAG

73 Arg Cys Ala Gln Gly Leu Arg Cys Leu Pro Arg Gln Asp Glu Glu Lys Pro Leu
 260 CGC TGC GCC CAG GGG CTG CGC TGC CTC CCC CGG CAG GAC GAG GAG AAG CCG CTG

91 His Ala Leu Leu His Gly Arg Gly Val Cys Leu Asn Glu Lys Ser Tyr Arg Glu
 314 CAC GCC CTG CTG CAC GGC CGC GGG GTT TGC CTC AAC GAA AAG AGC TAC CGC GAG

109 Gln Val Lys Ile Glu Arg Asp Ser Arg Glu His Glu Glu Pro Thr Thr Ser Glu
 368 CAA GTC AAG ATC GAG AGA GAC TCC CGT GAG CAC GAG GAG CCC ACC ACC TCT GAG

127 Met Ala Glu Glu Thr Tyr Ser Pro Lys Ile Phe Arg Pro Lys His Thr Arg Ile
 422 ATG GCC GAG GAG ACC TAC TCC CCC AAG ATC TTC CGG CCC AAA CAC ACC CGC ATC

145 Ser Glu Leu Lys Ala Glu Ala Val Lys Lys Asp Arg Arg Lys Lys Leu Thr Gln
 476 TCC GAG CTG AAG GCT GAA GCA GTG AAG AAG GAC CGC AGA AAG AAG CTG ACC CAG

163 Ser Lys Phe Val Gly Gly Ala Glu Asn Thr Ala His Pro Arg Ile Ile Ser Ala
 530 TCC AAG TTT GTC GGG GGA GCC GAG AAC ACT GCC CAC CCC CGG ATC ATC TCT GCA

181 Pro Glu Met Arg Gln Glu Ser Glu Gln Gly Pro Cys Arg Arg His Met Glu Ala
 584 CCT GAG ATG AGA CAG GAG TCT GAG CAG GGC CCC TGC CGC AGA CAC ATG GAG GCT

199 Ser Leu Gln Glu Leu Lys Ala Ser Pro Arg Met Val Pro Arg Ala Val Tyr Leu
 638 TCC CTG CAG GAG CTC AAA GCC AGC CCA CGC ATG GTG CCC CGT GCT GTG TAC CTG

217 Pro Asn Cys Asp Arg Lys Gly Phe Tyr Lys Arg Lys Gln Cys Lys Pro Ser Arg
 692 CCC AAT TGT GAC CGC AAA GGA TTC TAC AAG AGA AAG CAG TGC AAA CCT TCC CGT

235 Gly Arg Lys Arg Gly Ile Cys Trp Cys Val Asp Lys Tyr Gly Met Lys Leu Pro
 746 GGC CGC AAG CGT GGC ATC TGC TGG TGC GTG GAC AAG TAC GGG ATG AAG CTG CCA

253 Gly Met Glu Tyr Val Asp Gly Asp Phe Gln Cys His Thr Phe Asp Ser Ser Asn
 800 GGC ATG GAG TAC GTT GAC GGG GAC TTT CAG TGC CAC ACC TTC GAC AGC AGC AAC

271 Val Glu OP
 854 GTT GAG TGA TGCGTCCCCCCCCAACCTTTCCCTCACCCCCTCCCACCCCCAGCCCCGACTCCAGCCAG
 922 CGCCTCCCTCCACCCCAGGACGCCACTCATTTCATCTCATTTAAGGGAAAAATATATATCTATCTATTTGA
 993 GGAAACTGAGGACCTCGGAATCTCTAGCAAGGGCTCAACTTCGAAAATGGCAACAACAGAGATGCAAAAAG
1064 CTAAAAAGACACCCCCCCCCTTTAAATGGTTTTCTTTTTGAGGCAAGTTGGATGAACAGAGAAGGGAAGAG
1135 AGGAAGAACGAGAGGAAGAGAAGGGAAGGAAGTGTTTGTGTAGAAGAGAGAGAAAGACGAATAGAGTTAGG
1206 AAAAGGAAGACAAGCAGGTGGGCAGGAAGGACATGCACCGAGACCAGGCAGGGGCCCAACTTTCACGTCCA
1277 GCCCTGGCCTGGGGTCGGGAGAGGTGGGCGCTAGAAGATGCAGCCCAGGATGTGGCAATCAATGACACTAT
1348 TGGGGTTTCCCAGGATGGATTGGTCAGGGGGAGAAAGGAAAAGGCAAAACACTCCAGGACCTCTCCCGGAT
1419 CTGTCTCCTCCTCTAGCCAGCAGTATGGACAGCTGGACCCCTGAACTTCCTCTCTCCTCTTACCTGGGCAGAG
1490 TGTTGTCTCTCTCCCCAAATTTATAAAAACTAAAATGCATTCCATTCCTCTGAAAGCAAAACAAATTCATAAT
1561 TGAGTGATATTAAATAGAGAGGTTTTCGGAAGCAGATCTGTGAATATGAAAT
```

INSULIN-LIKE GROWTH FACTOR BINDING PROTEIN (IGFBP-5)

CROSS-REFERENCE TO RELATED APPLICATIONS

This application is a divisional of U.S. application Ser. No. 08/345,864, filed Nov. 28, 1994, now U.S. Pat. No. 6,500,635, which is a continuation of U.S. application Ser. No. 08/142,848, filed Oct. 26, 1993, now abandoned, and a continuation of U.S. application Ser. No. 07/638,628, filed Jan. 8, 1991, now abandoned, from which applications priority is claimed and which applications are incorporated by reference in their entireties.

BACKGROUND OF THE INVENTION

1. Field of the Disclosure

The present invention relates generally to production of polypeptides from recombinant DNA molecules encoding such polypeptides. More specifically, this invention relates to a new insulin-like growth factor binding protein (designated herein as IGFBP-5), recombinant DNA molecules encoding this polypeptide, and methods for producing IGFBP-5 from recombinant host cells.

2. Description of the Related Art

Insulin-like growth factors (IGFs) are low molecular weight polypeptide hormones with structural homology to proinsulin. Two different IGFs are known, namely IGF-I and IGF-II, which are mitogenic in vitro for a wide variety of cells in tissue culture. Both IGFs stimulate in vitro the growth of various tissues and in particular they induce collagen synthesis. IGF-I mediates the growth promoting effect of growth hormone in chondrogenesis and bone formation and is therefore essential for normal growth of an individual. This is demonstrated by the fact that pygmies and toy poodles are deficient in IGF-I but have normal growth hormone level in their serum. IGF-II is believed to play a key role in fetal development and nerve growth.

In addition to their primary effect on skeletal tissue IGFs also exhibit growth-stimulating functions on other tissues. Wound fibroblasts are known to produce IGFs which are effective in stimulating fibroblasts to grow and synthesize collagen, a structural protein normally required for wound healing. Vascularization of the wound tissue is also induced. Further, it has also been found that IGFs have an erythropoietin-like activity in that they induce hematopoiesis.

Recent studies have also demonstrated that IGFs produced by certain cancer cells, e.g. breast and kidney cancer cells, auto-stimulate the proliferation of cancer cells and the vascular and fibrous tissues required to support the growth of cancer tissues.

In addition to this, both IGFs show a spectrum of metabolic activities similar to those of insulin, in that they stimulate, in particular, the transport and metabolism of glucose. The biological effects of IGFs and insulin are mediated through their binding to specific receptors. In particular, both IGFs have the ability to bind to the insulin receptor with approximately 100-fold lower affinity than does insulin.

Both IGFs have a concentration in blood approximately a hundred-fold higher than that of insulin. Hypoglycemia is prevented by a regulatory mechanism which involves carrier proteins present in blood and able to form complexes with IGFs. Thus, IGFs circulate in the blood in the form of a complex which has no insulin-like activity.

Through their association with carrier proteins (hereinafter referred to as IGF binding proteins or IGFBPs), binding of IGFs to cell surface receptors is inhibited. It has also been demonstrated that another function of the IGF binding proteins is to increase the short half-life of IGFS, which are subjected to rapid proteolytic degradation when present in the free form in blood.

In accordance with the foregoing, IGFs may be useful in vitro to stimulate a) the growth of animals and humans with growth hormone deficiency, b) tissue regeneration, such as erythropoiesis and chondrogenesis, c) wound healing and d) the functions of various organs e.g. liver or kidney. As a result of their chondrogenesis stimulating activity, IGFs are of particularly suitable use for bone formation, e.g. in the treatment of osteoporosis.

IGFs for use in the above-referred treatments are advantageously administered to a subject in association with at least one IGF binding protein. Through their association with carrier proteins (hereinafter referred to as IGF binding proteins or IGFBPs), binding of IGFs to cell surface receptors is inhibited. It has also been demonstrated that another function of the IGF binding proteins is to increase the short half-life of IGFs, which are subjected to rapid proteolytic degradation when present in the free form in blood.

Administration of the combination of IGF and an IGF binding protein, rather than IGF alone, has beneficial effects including the prevention of hypoglycemia and possible mitogenic effects at injection sites and the prolongation of IGF half-life. Furthermore, it has been found that binding proteins are also useful for potentiating the erythropoietin like-effect of IGF-I. The binding proteins may also be useful for targeting IGFs to specific tissues.

When administered alone, i.e., without any IGF, the binding proteins may also be therapeutically useful for blocking the adverse effects of IGFs, such as those which occur when IGFs are produced in excess, e.g. free IGFs secreted by certain cancer cells e.g. hormone-producing cancer cells such as breast or kidney cancer cells. IGF binding protein therapy may also prevent blindness as a secondary effect of diabetic proliferation retinopathy. Indeed it has been shown that IGFs may be one of the factors stimulating endothelial and fibroblast proliferation in diabetic retinopathy.

Another therapeutic use of IGFBPs is the control of excessive growth in IGF binding protein-deficient subjects, since it is very likely that high IGF levels combined with abnormally low levels of binding protein are responsible for excessive growth.

Known forms of IGFBPs include IGFBP-1, having a molecular weight of approximately 30–40 kd in humans. See, e.g., Povoa, G. et al., Eur. J. Biochem (1984) 144:199–204, relates to IGFBP-1, isolated and purified from amniotic fluid; Koistinen, R. et al., Endocrinology (1986) 118:1375–1378, relates to IGFBP-1 isolated and purified from human placenta; Powell, D. R. et al., J. Chromatogr. (1987) 420:163–170, relates to a 30–40 kd IGFBP-1 isolated and purified from conditioned medium of hepatoma G2 (Hep-G2) cells; Lee, Y. L. et al., Mol. Endocrinol. (1988) 2:404–411, relates to an amino acid sequence of IGFBP-1 isolated from Hep-G2 cells; Brinkman, A. et al., The EMBO Journal (1988) 7: 2417–2423, relates to an IGFBP-1 placental cDNA library; Brewer, M. T. et al., Bioch. Biophys. Res. Com. (1988) 152:1289–1297, pertains to nucleotide and amino acid sequences for IGFBP-1 cloned from a human uterine decidua library; WO89/09792, published Oct. 19, 1990, Clemmons, D. R., et al., pertains to cDNA sequences and cloning vectors for IGFBP-1 and IGFBP-2; WO89/08667, published Sep. 21, 1989, Drop, L. S., et al., relates to an amino acid sequence of insulin-like-growth factor binding protein 1 (IGFBP-1); WO89/09268, published Oct. 5, 1989, Baxter, R. C., relates to a cDNA sequence of IGFBP-1 and methods of expression for IGFBP-1.

IGFBP-2 has a molecular weight of approximately 33–36 kd. See, e.g., Binkert, C. et al., The EMBO Journal (1989) 8:2497–2502, relates to a nucleotide and deduced amino acid sequence for IGFBP-2.

IGFBP-3 has a molecular weight of 150 kd. See, e.g., Baxter, R. C. et al., Bioch. Biopys. Res. Com. (1986) 139:1256–1261, pertains to a 53 kd subunit of IGFBP-3 that was purified from human serum; Wood, W. I. et al., Mol. Endocrinol. (1988) 2:1176–1185, relates to a full length amino acid sequence for IGFBP-3 and cellular expression of the cloned IGFBP-3 cDNA in mammalian tissue culture cells; WO90/00569, published Jan. 25, 1990, Baxter, R. C., relates to isolating from human plasma an acid-labile subunit (ALS) of (IGFBP) complex and, the particular amino acid sequence for ALS pertains to a subunit of IGFBP-3.

For nonhuman forms, see, e.g., Mottola, C. et al., Journ. of Biol. Chem. (1986) 261: 11180–11188, relates to a non-human form of IGFBP that was isolated in conditioned medium from rat liver BRL-3A cells and has a molecular weight of approximately 33–36 kd; Lyons, R. M. et al., Mol. Cell. Endocrinol. (1986) 45: 263–270, relates to a 34 kd cloned BRL-3A rat liver cell protein designated MCP; EPO Publ. No. 369 943, published May 23 1990, Binkert, C., et al., relates to a cDNA sequence of the rat BRL-3A binding protein and uses this sequence to screen three human cDNA libraries.

Mohan, S. et al., Proc. Natl. Acad. Sci. (1989) 86:8338–8342, relates to an N-terminal amino acid sequence for an IGFBP (designated therein as IGFBP-4 but, using Applicants' terminology as defined in the applications listed below, actually corresponding to IGFBP-5) isolated from medium conditioned by human osteosarcoma cells and Shimasaki, S. et al., Mol. Endocrinology (1990) 4:1451–1458, pertains to IGFBP cDNAs encoding an IGFBP (designated therein as IGFBP-4 but, using Applicants' terminology, actually corresponding to IGFBP-5) from rat and human.

Copending application Ser. No. 07/574,613, filed Aug. 28, 1990, which is co-owned by the present assignee, relates to IGFBP-6 and IGFBP-4 genetic material and amino acid sequences; copending application Ser. No. 07/576,648, filed Aug. 31, 1990, which is co-owned by the present assignee, relates to IGFBP-6 amino acid sequences; copending application Ser. No. 07/576,629, filed Aug. 31, 1990, which is co-owned by the present assignee, relates to IGFBP-6; copending application Ser. No. 07/577,391, filed Aug. 31, 1990, which is co-owned by the present assignee, relates to IGFBP-4 amino acid sequences; copending application Ser. No. 07/577,392, filed Aug. 31, 1990, which is co-owned by the present assignee, relates to genetic material encoding IGFBP-4.

Zapf, J. et al., J. of Biol. Chem. (1990) 265:14892–14898, pertains to four IGFBP's (IGFBP-2, IGFBP-3, a truncated form of IGFBP-3, and IGFBP-4) isolated from adult human serum by insulin-like growth factor (IGF) affinity chromatography and high performance liquid chromatography.

The existence of a number of different IGF-binding proteins indicates that these proteins may have different functions. Because it is possible to diagnose disease states and to modify in various different ways the biological activity of IGFs using the currently known binding proteins, there is significant interest in the discovery of new IGF-binding proteins having the same or different biological properties.

SUMMARY OF THE INVENTION

Accordingly, it is an object of the present invention to provide an IGF binding protein that differs from IGFBP-1, IGFBP-2, IGFBP-3, IGFBP-4, and IGFIBP-6.

It is further an object of the present invention to provide a new IGE binding protein using recombinant DNA molecules capable of expressing the new IGF binding protein (designated herein as IGFBP-5) in order to produce the binding protein.

These and other objects of the invention have been accomplished by providing a purified IGFBP selected from a group consisting of an IGFBP having an amino acid sequence which is at least 60%, preferably 70% and more preferably 85%, and most preferably 90%, homologous to the amino acid sequence of FIG. 1 and fragments thereof wherein the fragments are of a sufficient length to be unique to this binding protein (e.g., 10, 15, 20, or 25 consecutive amino acids of said sequence), and further wherein the purified binding protein is capable of binding to an antibody specific for IGFBP-5 or an insulin-like growth factor. Recombinantly produced binding protein molecules and antibodies that recognize the new binding protein are also part of the invention.

A significant advantage of producing IGFBP-5 by recombinant DNA techniques rather than by isolating IGFBP-5 from natural sources is that equivalent quantities of IGFBP-5 can be produced by using less starting material than would be required for isolating the binding protein from a natural source. Producing IGFBP-5 by recombinant techniques also permits IGFBP-5 to be isolated in the absence of some molecules normally present in cells that naturally produce IGFBP-5. Indeed, IGFBP compositions entirely free of any trace of human protein contaminants can readily be produced since the only human protein produced by the recombinant non-human host is the recombinant IGFBP. Potential viral agents from natural sources are also avoided. It is also apparent that recombinant DNA techniques can be used to produce IGFBP-5 polypeptide derivatives that are not found in nature, such as the variations described above.

BRIEF DESCRIPTION OF THE DRAWING

FIG. 1 is a schematic diagram showing amino acid and nucleotide sequences of a clone encoding human IGFBP-5.

DESCRIPTION OF SPECIFIC EMBODIMENTS

Novel compositions comprising recombinant proteins produced using sequences encoding IGFBP-5 and fragments derived thereof are provided, together with proteins isolated from natural sources as well as proteins expressed recombinantly, and methods for producing these proteins.

1. Definitions

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (0.1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986).

Standard abbreviations for nucleotides and amino acids are used in FIG. 1 and elsewhere in this specification.

As used herein, the term IGFBP-5 is an acronym for insulin-like growth factor binding protein 5. This protein, or a fragment thereof, is capable of binding to an antibody specific for IGFBP-5 or to an IGF factor. A cDNA encoding at least one form of IGFBP-5 is presented in FIG. 1. It is anticipated that other species of IGFBP-5 exist or that they can be created. Thus, IGFBP-5 refers to any of the naturally occurring forms of IGFBP-5, including the form shown in FIG. 1. In the sequence shown, the cleavage site for the mature protein may occur where indicated by arrow (a), resulting in a protein having a molecular weight of 29,018 Da. Additionally, another species of the protein may be cleaved where indicated by arrow (b), resulting in a protein having a molecular weight of approximately 28,500 Da.

Additionally, analogs are included within the definition and include truncated polypeptides (including fragments) and IGFBP-5-like polypeptides, e.g., mutants, that retain catalytic activity and preferably have a homology of at least 80%, more preferably 90%, and most preferably 95%. Typically, such analogs differ by only 1, 2, 3, or 4 codon changes. Examples include polypeptides with minor amino acid variations from the natural amino acid sequence of IGFBP-5; in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on the biological activity. Polypeptide molecules having substantially the same amino acid sequence as IGFBP-5 but possessing minor amino acid substitutions that do not substantially affect the ability of the IGFBP-5 polypeptide derivatives to interact with IGFBP-5-specific molecules, such as antibodies and IGF molecules, particularly IGF-I and especially IGF-II, are within the definition of IGFBP-5. Derivatives include aggregative conjugates with other IGF-BP molecules and covalent conjugates with unrelated chemical moieties. Covalent derivatives are prepared by linkage of functionalities to groups which are found in IGB-BP amino acid chains or at the– or C-terminal residues by means known in the art.

IGFBP-5-specific molecules include polypeptides such as antibodies that are specific for the IGFBP-5 polypeptide containing the naturally occurring IGFBP-5 amino acid sequence. By "specific binding polypeptide" is intended polypeptides that bind with IGFBP-5 and its derivatives and which have a measurably higher binding affinity for the target polypeptide, i.e., IGFBP-5 and polypeptide derivatives of IGFBP-5, than for other polypeptides tested for binding. Higher affinity by a factor of 10 is preferred, more preferably a factor of 100. Binding affinity for antibodies refers to a single binding event (i.e., monovalent binding of an antibody molecule). Specific binding by antibodies also means that binding takes place at the normal binding site of the molecule's antibody (at the end of the arms in the variable region).

Utilizing the sequence data in FIG. 1, as well as the denoted characteristics of IGFBP-5, it is within the skill of the art to obtain other DNA sequences encoding IGFBP-5. For example, the structural gene may be manipulated by varying individual nucleotides, while retaining the correct amino acid(s), or varying the nucleotides, so as to modify the amino acids, without loss of biological activity. Nucleotides may be substituted, inserted, or deleted by known techniques, including, for example, in vitro mutagenesis and primer repair. The structural gene may be truncated at its 3'-terminus and/or its 5'-terminus while retaining its biological activity.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

A "replicon" is any genetic element, e.g., a plasmid, a chromosome, a virus, a cosmid, etc. that behaves as an autonomous unit of polynucleotide replication within a cell; i.e., capable of replication under its own control. This may include selectable markers.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression, and may also include additional components whose presence is advantageous, for example, leader sequences and fusion partner sequences.

Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, cDNA, and recombinant polynucleotide sequences.

"PCR" refers to the technique of polymerase chain reaction as described in Saiki, et al., Nature 324:163 (1986); U.S. Pat. Nos. 4,683,195; and 4,683,202.

As used herein, x is "heterologous" with respect to y if x is not naturally associated with y in the identical manner; i.e., x is not associated with y in nature or x is not associated with y in the same manner as is found in nature.

"Homology" refers to the degree of similarity between x and y. It is expected that the overall homology between different species or forms of IGFBP-5 at the nucleotide level probably will be about 40% or greater, probably about 60% or greater, and even more probably about 80% to about 90% or greater. The correspondence between the sequence from one form to another can be determined by techniques known in the art. For example, they can be determined by a direct comparison of the sequence information of the polynucleotide. Alternatively, homology can be determined by hybridization of the polynucleotides under conditions which form stable duplexes between homologous regions (for example, those which would be used prior to $S_i$ digestion), followed by digestion with single-stranded specific nuclease(s), followed by size determination of the digested fragments.

As used herein, the term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

IGFBP-5, or polypeptide derivatives thereof, may be used for producing antibodies, either monoclonal or polyclonal, specific to IGFBP-5. These terms, and the methods for producing antibodies are known in the art.

"Recombinant host cells", "host cells", "cells", "cell lines", "cell cultures", and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation.

As used herein, the term "microorganism" includes prokaryotic and eukaryotic microbial species such as bacteria and fungi, the latter including yeast and filamentous fungi.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "purified" and "isolated" is meant, when referring to a polypeptide or nucleotide sequence, that the indicated molecule is present in the substantial absence of other biological macromolecules of the same type. The term "purified" as used herein preferably means at least 95% by weight, more preferably at least 99% by weight, and most preferably at least 99.8% by weight, of biological macromolecules of the same type present (but water, buffers, and other small molecules, especially molecules having a molecular weight of less than 1000, can be present).

2. Specific Modes for Carrying Out the Invention a. Source of IGFBP-5

IGFBP-5 is derivable form mammals, e.g., murine, porcine, equine, bovine, and human sources. All such sources are included within the definition of IGF-BP-5, as long as they comply with the required degree of homology.

IGF-BP-5 includes binding proteins purified from a tissue extract or from a conditioned culture medium as well as those obtained by recombinant means.

b. Purification of IGFBP-5

IGFBP-5 can be readily purified from blood and its components, such as serum and plasma and from cells genetically modified to produce IGFBP-5 or polypeptide derivatives thereof, by affinity chromatography using a monoclonal antibody specific for IGFBP-5. In addition to the use of antibody affinity chromatography, IGFBP-5 and polypeptide derivatives thereof can be purified by a variety of other widely known protein purification techniques (either alone or in combination) including immunoprecipitation, gel filtration, ion exchange chromatography, chromatofocusing, isoelectric focusing, selective precipitation, electrophoresis, and the like. Fractions isolated during purification procedures can be analyzed for the presence of IGFBP-5 or polypeptide derivatives of IGFBP-5 by immunoassays employing IGFBP-5-specific antibodies or IGFBP-5-specific bioassays. Detailed examples are provided below.

c. Isolation of IGFBP-5 Sequences

Isolation of nucleotide sequences encoding IGFBP-5 involves creation of either a genomic library prepared from cells encoding IGFBP-5 or preparation of a cDNA library from RNA isolated from cells expressing IGFBP-5. It will generally be preferable to create a cDNA library for isolation of IGFBP-5 coding nucleotide sequences so as to avoid any possible problems arising from attempts to determine intron/exon borders. Genetic libraries can be made in either eukaryotic or prokaryotic host cells. Widely available cloning vectors such as plasmids, cosmids, phage, YACs and the like can be used to generate genetic libraries suitable for the isolation of nucleotide sequences encoding IGFBP-5 or portions thereof.

d. Screening for the Presence of IGFBP-5 Sequences

Useful methods for screening genetic libraries for the presence of IGFBP-5 nucleotide sequences include the preparation of oligonucleotide probes based on the N-terminus amino acid sequence information from purified IGFBP-5 or purified internal fragments of purified IGFBP-5. By employing the standard triplet genetic code, oligonucleotide sequences of about 17 base pairs or longer can be prepared by conventional in vitro synthesis techniques so as to correspond to portions of IGFBP-5 for which the amino acid sequence has been determined by N-terminus analysis. The resultant nucleic acid sequences can be subsequently labeled with radionuclides, enzymes, biotin, fluorescers, or the like, and used as probes for screening genetic libraries.

Additional methods of interest for isolating IGFBP-5-encoding nucleic acid sequences include screening genetic libraries for the expression of IGFBP-5 or fragment thereof by means of IGFBP-5-specific antibodies, either polyclonal or monoclonal. A preferred technique involves the use of degenerate primers based on partial amino acid sequences of purified IGFBP-5 or on sequences from known related molecules and the polymerase chain reaction (PCR) to amplify gene segments between the primers. The gene can then be isolated using a specific hybridization probe based on the amplified gene segment, which is then analyzed from appropriate expression of protein. A detailed description of this technique is set forth in the examples that follow.

e. Sequencing Methods

Nucleotide sequences encoding IGFBP-5 can be obtained from recombinant DNA molecules recovered from IGFBP-5 genetic library isolates. The nucleotide sequence encoding IGFBP-5 can be obtained by sequencing the non-vector nucleotide sequences of these recombinant molecules. Nucleotide sequence information can be obtained by employing widely used DNA sequencing protocols, such as Maxim and Gilbert sequencing, dideoxy nucleotide sequencing, and the like. Examples of suitable nucleotide sequencing protocols can be found in Berger and Kimmel, *Methods in Enzymology Vol. 52, Guide to Molecular Cloning Techniques,* (1987) Academic Press. Nucleotide sequence information from several recombinant DNA isolates, including isolates from both cDNA and genomic libraries, may be combined so as to provide the entire amino acid coding sequence of IGFBP-5 as well as the nucleotide sequences of introns within the IGFBP-5 gene, upstream nucleotide sequences, and downstream nucleotide sequences.

Nucleotide sequences obtained from sequencing IGFBP-5 specific genetic library isolates are subjected to analysis in order to identify regions of interest in the IGFBP-5 gene. These regions of interest include open reading frames, introns, promoter sequences, termination sequences, and the like. Analysis of nucleotide sequence information is preferably performed by computer. Software suitable for analyzing nucleotide sequences for regions of interest is commercially available and includes, for example, DNASIS™ (LKB). It is also of interest to use amino acid sequence information obtained from the N-terminus sequencing of purified IGFBP-5 when analyzing IGFBP-5 nucleotide sequence information so as to improve the accuracy of the nucleotide sequence analysis.

f. Expression Systems

IGFBP-5 and polypeptide derivatives of IGFBP-5 can be expressed by recombinant techniques when a DNA sequence encoding the relevant molecule is functionally inserted into a vector. By "functionally inserted" is meant in proper reading frame and orientation, as is well understood by those skilled in the art. When producing a genetic construction containing a complete IGFBP-5 reading frame, a preferred starting material is a cDNA library isolate encoding IGFBP-5. Typically, the IGFBP-5 gene will be inserted downstream from a promoter and will be followed by a stop codon, although production as a hybrid protein followed by cleavage may be used, if desired. In general, host-cell-specific sequences improving the production yield of IGFBP-5 and IGFBP-5 polypeptide derivatives will be used and appropriate control sequences will be added to the expression vector, such as enhancer sequences, polyadenylation sequences, and ribosome binding sites.

i. Mammalian Systems

Once the appropriate coding sequence is isolated, it can be expressed in a variety of different expression systems; for example those used with mammalian cells, baculoviruses, bacteria, and yeast.

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, typically located within 100 to 200 bp upstream of the TATA box. An upstream promoter element determines the rate at which transcription is initiated and can act in either orientation [Sambrook et al. (1989) "Expression of Cloned Genes in Mammalian Cells."In *Molecular Cloning: A Laboratory Manual, 2nd ed.*].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will typically increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) Science 236:1237; Alberts et al. (1989) Molecular Biology of the Cell, 2nd ed.]. Enhancer elements derived from viruses may be particularly useful, because they typically have a broader host range. Examples include the SV40 early gene enhancer [Dijkema et al (1985) EMBO J. 4:761] and the enhancer/promoters derived from the long terminal repeat (LTR) of the Rous Sarcoma Virus [Gorman et al. (1982b) Proc. Natl. Acad. Sci. 79:6777] and from human cytomegalovirus [Boshart et al. (1985) Cell 41:521]. Additionally, some enhancers are regulatable and become active only in the presence of an inducer, such as a hormone or metal ion [Sassone-Corsi and Borelli (1986) Trends Genet. 2:215; Maniatis et al. (1987) Science 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell. The adenovirus tripartite leader is an example of a leader sequence that provides for secretion of a foreign protein in mammalian cells.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) Cell 41:349; Proudfoot and Whitelaw (1988) "Termination and 3' end processing of eukaryotic RNA. In Transcription and splicing (ed. B. D. Hames and D. M. Glover); Proudfoot (1989) Trends Biochem. Sci. 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In Molecular Cloning: A Laboratory Manual].

Some genes may be expressed more efficiently when introns (also called intervening sequences) are present. Several cDNAs, however, have been efficiently expressed from vectors that lack splicing signals (also called splice donor and acceptor sites) [see e.g., Gothing and Sambrook (1981) Nature 293:620]. Introns are intervening noncoding sequences within a coding sequence that contain splice donor and acceptor sites. They are removed by a process called "splicing," following polyadenylation of the primary transcript [Nevins (1983) Annu. Rev. Biochem. 52:441; Green (1986) Annu. Rev. Genet. 20:671; Padgett et al. (1986) Annu. Rev. Biochem. 55:1119; Krainer and Maniatis (1988) "RNA splicing." In Transcription and splicing (ed. B. D. Hames and D. M. Glover)].

Typically, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require transacting factors to replicate. For example, plasmids containing the replication systems of papovaviruses, such as SV40 [Gluzman (1981) Cell 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a procaryotic host for cloning and amplification. Examples of such mammalian-bacteria shuttle vectors include pMT2 [Kaufman et al. (1989) Mol. Cell. Biol. 9:946 and pHEBO [Shimizu et al. (1986) Mol. Cell. Biol. 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Systems

The polynucleotide encoding IGFBP-5 can also be inserted into a suitable insect expression vector, and is operably linked to the control elements within that vector. Vector construction employs techniques which are known in the art.

Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the IGFBP-5 DNA sequence into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif.

("MaxBac" kit). These techniques are generally known to those skilled in the art and fully described in Summers and Smith, *Texas Agricultural Experiment Station Bulletin* No. 1555 (1987) (hereinafter "Summers and Smith"), and incorporated by reference.

Prior to inserting the IGFBP-5 DNA sequence into the baculovirus genome, the above described components, comprising a promoter, leader (if desired), coding sequence of interest, and transcription termination sequence, are typically assembled into an intermediate transplacement construct (transfer vector). This construct may contain a single gene and operably liked regulatory elements; multiple genes, each with its own set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a procaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); E.P.O. Pub. Nos. 127,839 and 155,476; and the gene encoding the p10 protein Vlak et al., (1988), *J. Gen. Virol.* 69:765–.

DNA encoding suitable signal sequences can be derived from genes for secreted insect or baculovirus proteins, such as the baculovirus polyhedrin gene (Carbonell et al. (1988) *Gene*, 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA*, 82:8404; mouse IL-3, (Miyajima et al., (1987) *Gene* 58:273; and human glucocerebrosidase, Martin et al. (1988) *DNA*, 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment typically encodes a signal peptide comprised of hydrophobic amino acids which direct the translocation of the protein into the endoplasmic reticulum.

After insertion of the IGFBP-5 DNA sequence and/or the gene encoding the expression product precursor, an insect cell host is co-transformed with the heterologous DNA of the transfer vector and the genomic DNA of wild type baculovirus—usually by co-transfection. The promoter and transcription termination sequence of the construct will typically comprise a 2–5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2 156; and Luckow and Summers (1989)). For example, the insertion can be into a gene such as the polyhedrin gene, by homologous double crossover recombination; insertion can also be into a restriction enzyme site engineered into the desited baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. The beauty of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 µm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda*, and *Trichoplusia ni* (P.C.T. Pub. No. WO89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, e.g., Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain IGFBP-5 expression, recombinant host cells derived from the transformants are incubated under conditions which allow expression of the recombinant IGFBP-5 encoding sequence. These conditions will vary, dependent upon the host cell selected. However, the conditions are readily ascertainable to those of ordinary skill in the art, based upon what is known in the art.

iii. Bacterial Systems

Bacterial expression techniques are known in the art. A bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EPO Pub. Nos. 036 776 and 121 775]. The g-laotamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551, 433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO Pub. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli.*" In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO Pub. No. 219 237).

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) Nature 309:810]. Fusion proteins can also be made with sequences from the lacZ [Jia et al. (1987) Gene 60:197], trpE [Allen et al. (1987) J. Biotechnol. 5:93; Makoff et al. (1989) J. Gen. Microbiol. 135:11], and Chey [EPO Pub. No. 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated [Miller et al. (1989) Bio/Technology 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment typically encodes a signal peptide comprised of hydrophobic amino acids which direct the secretion of the protein from the cell. The protein is either secreted into the growth media (gram-positive bacteria) or into the periplasmic spece, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the E. coli outer membrane protein gene (ompA) [Masui et al. (1983), in: Experimental Manipulation of Gene Expression; Ghrayeb et al. (1984) EMBO J. 3:2437] and the E. coli alkaline phosphatase signal sequence (phoA) [Oka et al. (1985) Proc. Natl. Acad. Sci. 82:7212]. As an additional example, the signal sequence of the alpha-amylase gene from various Bacilus strains can be used to secrete heterologous proteins from B. subtilis [Palva et al. (1982) Proc. Natl. Acad. Sci. USA 79:5582; EPO Pub. No. 244 042].

Typically, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in E. coli as well as other biosynthetic genes.

Typically, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a procaryotic host either for expression or for cloning and amplification. In addition, a replicoin may be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bactedrial chromosome. For example, integrating vectors constructed with DNA from various Bacillus strains integrate into the Bacillus chromosome (EPO Pub. No. 127 328). Integrating vectors may also be comprised of bacteriophage or transposon sequences.

Typically, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) Annu. Rev. Microbiol. 32:469]. Selectable markers may also include biosynthetic genes, such as those in the histidine, tryptophan, and leucine biosynthetic pathways.

Alternatively, some of the above described components can be put together in transformation vectors. Transformation vectors are typically comprised of a selectable market that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: Bacillus subtilis [Palva et al. (1982) Proc. Natl. Acad. Sci. USA 79:5582; EPO Pub. Nos. 036 259 and 063 953; PCT WO 84/04541], Escherichia coli [Shimatake et al. (1981) Nature 292:128; Amann et al. (1985) Gene 40:183; Studier et al. (1986) J. Mol. Biol. 189:113; EPO Pub. Nos. 036 776, 136 829 and 136 907], Streptococcus cremoris [Powell et al. (1988) Appl. Environ. Microbiol. 54:655]; Streptococcus lividans [Powell et al. (1988) Appl. Environ. Microbiol. 54:655], Streptomyces lividans [U.S. Pat. No. 4,745,056].

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., [Masson et al. (1989) FEMS Microbiol. Lett. 60:273; Palva et al. (1982) Proc. Natl. Acad. Sci. USA 79:5582; EPO Pub. Nos. 036 259 and 063 953; PCT WO 84/04541, Bacillus], [Miller et al. (1988) Proc. Natl. Acad. Sci. 85:856; Wang et al. (1990) J. Bacteriol. 172:949, Campylobacter], [Cohen et al. (1973) Proc. Natl. Acad. Sci. 69:2110; Dower et al. (1988) Nucleic Acids Res. 16:6127; Kushner (1978) "An improved method for transformation of Escherichia coli with ColE1-derived plasmids. In Genetic Engineering: Proceedings of the International Symposium on Genetic Engineering (eds. H. W. Boyer and S. Nicosia); Mandel et al. (1970) J. Mol. Biol. 53:159; Taketo (1988) Biochim. Biophys. Acta 949:318;

*Escherichia*], [Chassy et al. (1987) *FEMS Microbiol. Lett.* 44:173 Lactobacillus]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation o*Streptococcus* lactis by electroporation, in: *Streptococcal Genetics* (ed. J. Ferretti and R. Curtiss III); Perry et al. (1981) *Infec. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

iv. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EPO Pub. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Pub. No. 329 203). The yeast PHO5 gene, encoding acid phosphatase, also provides useful promoter sequences [Myanohara et al. (1983) *Proc. Natl. Acad. Sci. USA* 80:1).

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EPO Pub. No. 164 556). Furthermore, a yeast promoter can include naturally occurring promoters of non-yeast origin that have the ability to bind yeast RNA polymerase and initiate transcription. Examples of such promoters include, inter alia, (Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes i the Yeast *Saccharomyces cerevisiae*," in: *Plasmids of Medical, Environmental and Commercial Importance* (eds. K>N>Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Typically, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EPO Pub. No. 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (see, e.g., PCT WO 88/024066). This system is a preferred system for producing IGFBP-5.

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell.

DNA encoding suitable signal sequences can be derived from genes for secreted yeast proteins, such as the yeast invertase gene (EPO Pub. No. 012 873; JPO Pub. No. 62,096,086) and the A-factor gene (U.S. Pat. No. 4,588, 684). Alternatively, leaders of non-yeast origin, such as an interferon leader, exist that also provide for secretion in yeast (EPO Pub. No. 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) (U.S. Pat. Nos. 4,546,083 and 4,870,008; EPO Pub. No. 324 274). Additional leaders employing an alpha-factor leader fragment that provides for secretion include hybrid alpha-factor leaders made with a presequence of a first yeast, but a pro-region from a second yeast alphafactor. (See e.g., PCT WO 89/02463.)

Typically, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Typically, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 [Botstein et al. (1979) Gene 8:17–24], pCl/1 [Brake et al. (1984) Proc. Natl. Acad. Sci USA 81:4642–4646], and YRp17 [Stinchcomb et al. (1982) J. Mol. Biol. 158:157]. In addition, a replicon may be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Enter a high or low copy number vector may be selected, depending upon the effect of the vector and the foreign protein on the host. See e.g., Brake et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) Methods in Enzymol. 101:228–245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) Proc. Natl. Acad. Sci. USA 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Typically, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) Microbiol, Rev. 51:351].

Alternatively, some of the above described components can be put together into transformation vectors. Transformation vectors are typically comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts:Candida albicans [Kurtz, et al. (1986) Mol. Cell. Biol. 6:142], Candida maltosa [Kunze, et al. 91985) J. Basic Microbiol. 25:141], Hansenula polymorpha [Gleeson, et al. (1986) J. Gen. Microbiol. 132:3459; Roggenkamp et al. (1986) Mol. Gen. Genet. 202:302], Kluyveromyces fragilis [Das, et al. (1984) J. Bacteriol. 158:1165], Kluyveromyces lactis [De Louvencourt et al. (1983) J. Bacteriol. 154:737; Van den Berg et al. (1990) Bio/Technology 8:135], Pichia guillerimondii [Kunze et al. (1985) J. Basic Microbiol. 25:141], Pichia pastoris [Cregg, et al. (1985) Mol. Cell. Biol. 5:3376; U.S. Pat. Nos. 4,837,148 and 4,929,555), Saccharomyces cerevisiae [Hinnen et al. (1978) Proc. Natl. Acad. Sci. USA 75:1929; Ito et al. (1983) J. Bacteriol. 153:163], Schizosaccharomyces pombe [Beach and Nurse (1981) Nature 300:706], and Yarrowia lipolytica [Davidow, et al. (1985) Curr. Genet. 10:380471 Gaillardin, et al. (1985) Curr. Genet. 10:49].

Methods of introducing exogenous DNA into yeast hosts are well-known in the art, and typically include either the transformation of spheroplasts or of intact yeast cells treated with alkali cations. Transformation procedures usually vary with the yeast species to be transformed. See e.g., [Kurtz et al. (1986) Mol. Cell. Biol. 6:142; Kunze et al. 91985) J. Basic Microbiol. 25:141; Candida]; [Gleeson et al. 91986) J. Gen. Microbiol. 132:3459; Roggenkamp et al. (1986) Mol. Gen. Genet. 202:302; Hansenula]; [Das et al. (1984) J. Bacteriol. 158:1165; De Louvencourt et al. (1983) J. Bacteriol. 154:1165; Van den Berg et al. (1990) Bio/Technology 8:135; Kluyveromyces]; [Cregg et al. (1985) Mol. Cell. Biol. 5:3376; Kunze et al. (1985) J. Basic Microbiol. 25:141; U.S. Pat. Nos. 4,837,148 and 4,929,555; Pichia]; [Hinnen et al. (1978) Proc. Natl. Acad. Sci. USA 75;1929; Ito et al. (1983) J. Bacteriol. 153:163 Saccharomyces]; [Beach and Nurse (1981) Nature 300:706; Schizosaccharomyces]; [Davidow et al. (1985) Curr. Genet. 10:39; Gaillardin et al. (1985) Curr. Genet. 10:49; Yarrowia].

g. Production of Antibodies to IGFBP-5

Antibodies specific for IGFBP-5 are produced by immunizing an appropriate vertebrate host, e.g., rabbit, with purified IGFBP-5 or polypeptide derivatives of TGFBP-5, by themselves or in conjunction with a conventional adjuvant. Usually, two or more immunizations will be involved, and blood or spleen will be harvested a few days after the last injection. For polyclonal antisera, the immunoglobulins can be precipitated, isolated and purified by a variety of standard techniques, including affinity purification using IGFBP-5 attached to a solid surface, such as a gel or beads in an affinity column. For monoclonal antibodies, the splenocytes normally will be fused with an immortalized lymphocyte, e.g., a myeloid cell line, under selective conditions for hybridoma formation. The hybridomas can then be cloned under limiting dilution conditions and their supernatants screened for antibodies having the desired specificity. Techniques for producing antibodies are well known in the literature and are exemplified by the publication Antibodies: A Laboratory Manual (1988) eds. Harlow and Lane, Cold Spring Harbor Laboratories Press, and U.S. Pat. Nos. 4,381,292, 4,451,570, and 4,618,577.

For both in vivo use of antibodies to IGFBP-5 and anti-idiotype antibodies and diagnostic use, it may be preferable to use monoclonal antibodies. Monoclonal anti-virus particle antibodies or anti-idiotype antibodies can be produced as follows. The spleen or lymphocytes from an immunized animal are removed and immortalized or used to prepare hybridomas by methods known to those skilled in the art. To produce a human-human hybridoma, a human lymphocyte donor is selected. Epstein-Barr virus (EBV) can be used to immortalize human lymphocytes or a human fusion partner can be used to produce human-human hybridomas. Primary in vitro immunization with peptides can also be used in the generation of human monoclonal antibodies. Antibodies secreted by the immortalized cells are screened to determine the clones that secrete antibodies of the desired specificity.

h. Diagnostic Methods using Antigens, Genetic Material, of Antibodies

The compositions comprising antigens or antibodies of the present invention, as well as the genetic material, can be used in diagnostic assays. Among the biologically useful information that can be obtained is excessive binding protein levels due to the presence of tumors, that result in increased production of either IGF or one of the IGFBP binding proteins (since the binding proteins are produced in the presence of excess IGF). Additionally, a number of known disorders can be related to IGF concentrations. For example, some types of osteoporosis is related to IGF levels. Additionally, the binding proteins can be used in the identification, production, and purification of recombinantly produced IGFs. Methods for detecting the presence of IGFBP-5 comprise analyzing a biological sample such/a blood sample, cerebrospinal fluid, or tumor or bone tissue.

Typically, methods for detecting analytes such as binding proteins of the invention are based on immunoassays. Such techniques are well known and need not be described here in detail. Examples include both heterogeneous and homogeneous immunoassay techniques. Both techniques are based on the formation of an immunological complex between the binding protein and a corresponding specific antibody. Heterogeneous assays for IGFBP-5 typically use a specific monoclonal or polyclonal antibody bound to a solid surface. Sandwich assays are increasingly popular. Homogeneous assays, which are carried out in solution without the presence of a solid phase, can also be used, for example by determining the difference in enzyme activity brought on by binding of free antibody to an enzyme-antigen conjugate. A number of suitable assays are disclosed in U.S. Pat. Nos. 3,817,837, 4,006,360, 3,996,345.

The solid surface reagent in the above assay is prepared by known techniques for attaching protein material to solid support material, such as polymeric beads, dip sticks, or filter material. These attachment methods generally include non-specific adsorption of the protein to the support or covalent attachment of the protein, typically through a free amine group, to a chemically reactive group on the solid support, such as an activate carboxyl, hydroxyl, or aldehyde group.

In a second diagnostic configuration, known as a homogeneous assay, antibody binding to an analyte produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

i. Diagnostic Applications using Genetic Probes

The genetic material of the invention can itself be used in numerous assays as probes for genetic material present in naturally occurring materials. The analyte can be a nucleotide sequence which hybridizes with a probe comprising a sequence of (usually) at least about 16 consecutive nucleotides, usually 30 to 200 nucleotides, up to substantially the full sequence of the sequences shown above (cDNA sequences). The analyte can be RNA or cDNA. The sample is typically as described in the previous section. A positive result is generally characterized as identifying a genetic material comprising a sequence at least about 70% homologous to a sequence of at least 12 consecutive nucleotides of the sequences given herein, usually at least about 80% homologous to at least about 60 consecutive nucleotides within the sequences, and may comprise a sequence substantially homologous to the full-length sequences. In order to detect an analyte, where the analyte hybridizes to a probe, the probe may contain a detectable label. Probes that are particularly useful for detecting binding proteins are based on conserved regions of these proteins, particularly from amino acids 181–191 (PNCD) and amino acids 212–215 (CWCV) of IGFBP-5. These amino acids are highly conserved in all of the related IGF binding proteins. Only 4GFBP-1 has a difference, an N for a D at position 191.

One method for amplification of target nucleic acids, for later analysis by hybridization assays, is known as the polymerase chain reaction or PCR technique. The PCR technique can be applied to detecting IGFBP-5 of the invention in suspected samples using oligonucleotide primers spaced apart from each other and based on the genetic sequence set forth herein. The primers are complementary to opposite strands of a double stranded DNA molecule and are typically separated by from about 50 to 450 nt or more (usually not more than 2000 nt). This method entails preparing the specific oligonucleotide primers and then repeated cycles of target DNA denaturation, primer binding, and extension with a DNA polymerase to obtain DNA fragments of the expected length based on the primer spacing. Extension products generated from one primer serve as additional target sequences for the other primer. The degree of amplification of a target sequence is controlled by the number of cycles that are performed and is theoretically calculated by the simple formula 2n where n is the number of cycles. Given that the average efficiency per cycle ranges from about 65% to 85%, 25 cycles produce from 0.3 to 4.8 million copies of the target sequence. The PCR method is described in a number of publications, including Saiki et al., Science (1985) 230:1350–1354; Saiki et al., Nature (1986) 324:163–166; and Scharf et al., Science (1986) 233:1076–1078. Also see U.S. Pat. Nos. 4,683,194; 4,683,195; and 4,683,202.

The invention includes a specific diagnostic method for determination if IGFBP-5 based on selective amplification of IGFBP-5-encoding DNA fragments. This method employs a pair of single-strand primers derived from non-homologous regions of opposite strands of a DNA duplex fragment selected from the sequences set forth in FIG. 1. These "primer fragments," which form one aspect of the invention, are prepared from IGFBP-5 fragments such as described above. The method follows the process for amplifying selected nucleic acid sequences as disclosed in U.S. Pat. No. 4,683,202, as discussed above.

Assay for Biological Properties of IGFBP-5

The property of binding to an insulin-like growth factor is one of the biological activities of the proteins of the invention. These proteins may be conveniently tested in a binding assay using IGF-I [Rinderknecht, E. and Humbel, R. E., J. Biol. Chem. (1978) 253 27691] or IGF-II [Rinderknecht, E. and Humbel, R. E., FEBS (1978) 89: 283], preferably IGF-II, in a labelled, e.g., iodinated form. For example, such an assay may conveniently include performing a gel electrophoresis (SDS-PAGE) of the proteins of the invention, followed by a western blot of the gel, then incubating the blot in the presence of $[^{125}I]$IGF-I or II, washing the blot to remove free IGF-I or -II, and detecting the radioactivity on the blot.

Uses of IGFBP-5

Therapeutic applications of the binding proteins of the invention include its use as a single therapeutic agent and its use in combination with an IGF, the latter use being preferred.

When used in combination with an IGF, a binding protein of the invention is suitable for use in the indications above mentioned, primarily as a growth inducing, tissue regenerating or would healing agent.

Accordingly, the invention provides:

i) use of a binding protein of the invention together with IGF in free or fixed combination for stimulating the growth of a subject, tissue or organ regeneration or wound healing, or ii) a method of stimulating the growth of a subject, tissue or organ regeneration or wound healing in a subject which comprises administering a therapeutically effective amount of a binding protein of the invention together with a therapeutically effective amount of an IGF to a patient in need of such treatment, or iii) a pharmaceutical composition for stimulating the growth of a subject, tissue or organ regeneration or wound healing which comprises a binding protein of a invention together with an IGF and with a pharmaceutically acceptable carrier or diluent, or iv) a package containing separate until dose forms of a binding protein of the invention and an IGF, together with instructions for mixing or concomitant administration.

In association with an IGF, a binding protein of the invention is of special interest for mediating chondrogenesis or hematopoieses. This may be shown in the following tests A to C.

A) An IGF increases bone formation as indicated by e.g. an increased incorporation of [3H]-proline into collagen and non-collagen proteins in fetal rat calvaria. A synergistic effect occurs when an IGF is used in the presence of a binding protein of the invention. Organ cultures of rat calvaria are prepared by dissecting frontal and parietal bones from 21-day old fetal rats, splitting along the sagittal suture and culturing according to the method of Kream et al. (Endocrinology (1985) 116. 296). A binding protein or IGF is added in doses from 10 to 200 ng ml of cultures. When they are added to combination to each other the molar ratio is 1:1. Culturing is effected for 24 to 48 hours. To quantitate the incorporation of [3H]proline into collagenase-digestible protein and non-collagen protein, bone homogenates are digested with bacterial collagenase according to the method of Diegelman R. and Peterkofsky (Dev. Biol. (1972) 28:443) and modified by Kream et al. (Endocrinology (1985) 116:296).

B) An IGF decreases bone resorption as indicated by a decrease in release of [45]Ca from bone. A synergistic effect occurs when an IGF is used in the presence of a binding protein of the invention. The test is effected according to the principles of Raisz (J. Clin. Invest. (1965) 44:103). Pregnant rats are injected s.c. with [45]Ca on the eighteenth day of gestation. An IGF, alone or in the presence of a binding protein of the invention, is injected at a dose of 10 ng to 200 ng per animal. The binding protein is added so that the molar ratio of IGF is 1:1. On day nineteen, the animals are sacrified, the fetuses removed. The mineralized shafts of the radii and ulnae are dissected and placed in culture. Resorption is quantitated on the basis of release of [45]Ca from the bone explants.

C) The IGF-binding proteins of the invention as well as other IGF-binding proteins potentiate the erythropoietin-like effect of IGF-I. This may be, in particular, demonstrated by testing IGF-I, e.g. 10 ng/ml IGF-I, alone and in combination with the mature IGF binding protein of FIG. 1, e.g. a 50 yml aliquot of a supernatant derived from a culture of a CHO cell line expressing the mature IGF binding protein of FIG. 1, in a CFU-E assay as described in Fagg, B. Roitsch, C.A. Cell, Physiol. (1986) 126:1. Whereas the result obtained with IGF-binding protein alone is not significantly different from the control, a synergistic effect of the combination is seen when compared to IGF-I alone.

Further, the mitogenic activity of an IGF combined with a binding protein of the invention may be tested as follows: The incorporation of [$^3$H] methyl-thymidine into CCL 39 cells (Chinese hamster lung fibroblasts) in culture is measured as described by Plouet et al. Cell. Miol. (1984) 30:105. In this assay, cell line CCI 39 is seeded in a plate at 40 000 cells per well in 0.5 ml MEM culture medium (Gibco) containing 10% fetal calf serum 0.1% penicillin, 0.4% streptomcyin and 0.5% fungizone. After 72 hours incubation at 37° C. in an atmosphere loaded with 5% $CO_2$. Cells are washed with MEM medium in the absence of fetal call serum and then cultured in his medium for 20 hours. At this stage, the cell culture is confluent and an IGF or a binding protein or both together are inoculated each at a dose of 10 ng to 200 ng culture medium. When added together the molar ratio must be 1:1. The test sample is incubated at 37° C. for 24 hours and then added with 1 mCi [$^3$H] methylthymidine in 10 ml PBS. After 4 hours incubation the incorporation of methylthymidine is stopped washing cells with PBS. Cells are fixed with 0.5 ml trichloroacetic acid (5%) for 30 min. washed with water and finally lysed with 0.5 ml of NaOH 0.1M for 2 hours at 37° C. 0.5 ml of lysate is transferred into a scintillation flask and mixed with 3 ml of scintillation liquid for measuring b-radioactivity. The binding protein potentiates the mitogenic activity of IGF although the radioactivity level that is measured when a binding protein is used alone is not substantially different from that of the control sample.

More particularly a binding protein of the invention, in combination with an IGF is useful a) for treating hypopituitarism. Laron-type dwarfism, osteoporosis, anemias especially complications following an chronic renal failure and liver or kidney deficiency and b) for promoting healing of wounds such as ulcers and vurns or those occuring in accidental events or resulting from surgery.

For use in association with a binding protein of the invention. IGF is preferably selected from IGF-I as described in Rinderknecht, E. and Humbel, R. E., J. Biol. Chem. (1978) 253:2769. IGF-II as described in Rinderknecht, E. and Humbel, R. E., FEBS (1978) 89:283 and any derivative or fragment of IGF-I and IGF-II having an insulin-like growth factor activity. Most preferably, this is IGF-II.

For use in association with an IGF, a binding protein of the invention is preferably a protein which is from 85% to 100% homologous with pre IGF-BP or IGF-BP as shown in FIG. 1.

When not associated with IGFS, binding proteins of the invention have further therapeutic applications in any physiological disorders resulting from an excessive production of free IGF, e.g. IGF-producing cancers such as breast or kidney cancer, diabetic proliferative retinopathy or abnormal growth of tall children with high serum level of free IGF.

Accordingly, the invention also provides:

(a) the use of a binding protein of the invention for treating physiological disorders resulting from an excessive production of free IGF by a mammalian, for example human body, e.g. IGF-producing cancers, diabetic retinopthy or abnormal growth of tall subjects, or (b) a method of treating physioligical disorders resulting from an excessive production of free IGF, e.g. IGF-producing cancers, diabetic retinopathy or abnormal growth of a subject which comprises administering a therapeutically effective amount of aa binding protein of the invention to a subject in need of such treatment, or (c) a pharmaceutical composition for treating physiological disorders resulting from an excessive production of free IGF, e.g. IGF-producing cancers, diabetic retinopathy or abnormal growth of a subject which comprises a binding protein of the invention in association with a pharmaceutically acceptable carrier or diluent, or (iv) a method of delivering IGFs to specific organs or tissues based on the differential binding properties of IGFBP-5, as indicated by biological testing.

Fragments of mutated forms of the pre-IGF-BP or IGF-BP as shown in FIG. 1 are of particular value for treating the physiological disorders resulting from an excessive production of free IGF in the human body.

A binding protein of the invention, alone or in combination with an IGF, may be administered by any conventional route suitable for peptides, or particular enterally, e.g. in the form of tablets or capsules or, preferably parenterally, e.g. subcutaneously or intravenously in the form of injections of infusions. Further, it may be also used topically, e.g. in the form of ointments or suspensions when used, e.g. as a wound healing agent.

For all the above indications the appropriate dosage will of course vary depending upon, for example, the nature and severity of the disorder to be treated and the mode of administration. For example, satisfactory results may be obtained in the treatment of osteoporosis or anemia at daily dosages from about to 0.1 mg/kg to 40 mg/kg body weight, preferably from about 0.5 mg/kg to about 20 mg/kg body weight of a binding protein of the invention. In larger mammals, for example humans, as indicated daily dosage is from about 5 mg conveniently administered parenterally, for example once a day. For wound healing, a daily dose of from 0.1 to 10 mg of a protein of the invention per cm2 wound area is suitably indicated in larger mammals, for example humans. This is conveniently administered once a day. When used in combination with an IGF, the molar ratio of the binding protein to IGF is preferably from 0.1:1 to 5:1, more preferably from 0.5:1 to 2:1, most preferably 1:1.

Pharmaceutical compositions of the invention may be manufactured in conventional manner.

Other uses for the binding proteins of the invention include various uses in the production of IGF molecules by recombinant techniques. The binding proteins of the invention can be used to detect yeast-produced IGF in native (active) conformation (as opposed to inactivated forms). Additionally, the proteins of the invention can be used as carrier (possibly in the form of co-expressed proteins) in the production of IGF. As the binding protein stabilized IGF in vivo, they are expected to do the same in vitro. The binding proteins can also be used to purify IGF produced in yeast by attaching them to a solid surface (such as in affinity chromatography).

Although the invention has been described with reference to particular embodiments, methods, construction, and use, it will be apparent to those skilled in the art that various changes and modifications can be made without departing from the invention.

3. Examples

Tissues

Human osteosarcoma tissue was obtained from Dr. Marshall Urist Univ. of California, Los Angeles).

RNA Isolation

RNA was isolated by the guanidinium thiocyanate method [Chirgiven, J. M. et al. (1979) Biochemistry 18: 5294–5299] with modification [Freeman, G. J. et al. (1983) Proc. Natl. Acad. Sci. USA 80: 4094–4098). Poly (A)$^+$ RNA was purified by a single fractionation over oligo(dT)-cellulose {Aviv, H. and Leder, P. (1972) Proc. Natl. Acad. Sci USA 69: 1408–1412].

Oligonucleotide Synthesis

Oligonucleotide adapters, probes and primers were synthesized by the phosphoramidite method with an Applied Biosystems model 380A synthesizer, purified by polyacrylamide gel electrophoresis and desalted on Sep-Pak $C_{18}$ cartridges (Waters, Milford, Mass.).

A 14-mer oligonucleotide (5' CCTGTAGATCTCCG 3') and 18-mer oligonucleotide (5' AATTCGGAGATCTA-CAGG 3') were synthesized and used as the EcoRI adaptors for the cDNA library constructed in λZAPII. The 14-mer was phosphorylated [Maniatis, T. et al. (1982). Molecular Cloning, a Laboratory Manual (Cold Spring Harbor Laboratory, Cold Spring Harbor, N.Y.)], then immediately heated to 95° C. for 15 minutes to inactivate the polynucleotide kinase. The adaptors also contain an internal BglII site.

The two consensus PCR primers used to identify IGFBP-5 were a sense primer consisting of a mixture of 32 24-mers (5'AGATCTAATTCGCCXAA(C/T)TG(C/T)(A/G)A 3') and an antisense primer consisting of a mixture of 16 25-mers (5' AGATCTAAGCTTCXAC(A/G)CACCA(A/G)CA 3') where X denotes all four deoxynucleotides. EcoRI and HindIII sites were included in the sense and antisense primers, respectively, to allow for subcloning of the PCR products into M13 sequencing vectors.

The IGFBP-5 probes used to screen the cDNA library were two 19-mers, (5' GCAAAGGATTCTACAAGAG 3') and (5'CAAACCTTCCCGTGGCCGC 3')

PCR Amplification

The PCR reactions were performed with the PCR kit (Perkin Elmer Cetus) according to the instructions of the supplier using the PCR primers described above at a final concentration of 8 μM. The template cDNA was synthesized from 2.5 μg of human osteosarcoma (Ost2) poly(A)$^+$ RNA. The conditions of cDNA synthesis were identical to those for first strand cDNA synthesis (see construction of cDNA library). The cDNA was fractionated on Biogel A-15m, recovered by ethanol precipitation and resuspended in 100 μl of sterile water. 1 μl of cDNA template was used for the PCR reaction. 35 cycles of PCR were performed in a Perkin Elmer Cetus DNA thermal cycler. The first 10 cycles consisted of a 94° C., 1 minute denaturation step, a 33° C., 1 minute annealing step and a 33° C., 1 minute extension step. The next 25 cycles consisted of a 94° C., 1 minute denaturation step, a 55° C., 1 minute annealing step and a 72° C., 1 minute extension step. The final extension step of the last cycle was 7 minutes. The sample was extracted once with phenol/chloroform/isoamylalcohol (1:1:0.04), once with chloroform/isoamylalcohol (24:1) and recovered by ethanol precipitation. The PCR DNA product was then incubated for 20 minutes at 37° C. with 10 units of DNA polymerase I, Klenow fragment in 10 mM Tris-HCl pH 7.5, 10 mM $MgCl_2$, 50 mM NaCl, 1 mM ditheothreitol and 40 μM each of dATP, dGTP, dTTP and dCTP. The sample was extracted as above, recovered by ethanol precipitation, digested with Eco RI and Hind III, and fractionated by electrophoresis on a 7% acrylamide, 1×TBE (Tris/borate/EDTA) gel. DNA migrating between 80–100 base pairs was excised from the gel; passively eluted from 16 hours with gentle shaking in 10 mM Tris-hydrochloride pH 7.5, 1 mM EDTA, purified by passage over an elutip-D column as described by the supplier (Schleicher and Schuell), ligated to an EcoRI and HindIII cut M13 sequencing vector (mp18) and introduced into E. coli strain DH5αF'.

Construction of the cDNA Library

A λZAPII/human osteosarcoma cDNA library was constructed from human osteosarcoma poly(A)+ RNA as described in Zapf et al. (1990) J. Biol. Chem. 265: 14892–14898. A library of 1.75×10$^7$ independent recombinant clones was obtained.

Screening of the cDNA Library

Approximately 300,000 recombinant phages from the Ost4 cDNA library were plated (50,000 phages/137 mm diameter plate) in E. coli BB4 and grown for 5–6 hours at 5 37° C. The phages were transferred onto nitrocellulose filters (Millipore, FIAFT 137), processed [Benton, W. D., and Davis, R. W. (1977) Anal. Biochem. 137: 266–267] and screened with two BP6 probes. The probes were labeled with $T_4$ polynucleotide kinase and [γ$^{32}$P]ATP [Maniatis, T., et al. (1982) Molecular Cloning, A Laboratory Manual (Cold Spring Harbor Laboratory, Cold Spring Harbor, N.Y.)] to a specific activity of 1–2×10$^8$ cpm/μg. The filters were prehybridized for 1–2 hours at 3700 as described in Zapf et at (1990) J. Biol. Chem. 26S: 14892–14898. Labeled probe was added to a concentration of 10$^6$ cpm/ml and hybridization was continued overnight at 37° C. with gentle shaking. The filters were washed in 2×SSC (1×SSC=0.15M sodium chloride/0.015M sodium citrate, pH 7), 0.1% SDS at 50° C. and exposed overnight at −80° C. to Kodak XAR-2 films with a Du Pont Lightning Plus intensifying screen. Areas of plaques giving duplicate signals were picked, replicated, and rescreened until pure plaques were obtained.

Plasmid Isolation, Subcloning and Sequencing

Bluescript SK(−) plasmids containing IGFBP-5 cDNA inserts were released from λZAP by the M13 rescue/excision protocol described by the supplier (Stratagene). Plasmid DNA was isolated by the alkaline lysis method [Maniatis, T. et al. (1982) Molecular Cloning, A Laboratory Manual (Cold Spring Harbor Laboratory, Cold Spring Harbor, N.Y.). The inserts were excised from the Bluescript SK(−) vector by BglII or EcoRI digestion and fractionated by agarose gel electrophoresis. Inserts were cut out from the gel and eluted for 12 hours with gentle shaking in 10 mM Tris-hydrochloride pH 7.5, 1 mM EDTA (TE), purified over an elutip-D column (see above) and subcloned into a M13 sequencing vector [Yanish-Perron, C. et al. (1985) Gene 33: 103–119]. DNA sequencing was performed by the dideoxy chain termination method (Sanger, F. et al. (1977) Proc. Natl. Acad. Sci. USA 74: 5463–5467) using M13 primers as well as specific internal primer. Ambiguous regions were resolved using 7-deaza-2-deoxyguanosine-triphosphate [Barr, P. J. et al. (1986) Biotechniques 4: 428–432] and Sequenase (US Biochemicals).

Northern Blot Analysis

Poly(A)+ RNA was fractionated on 1.4% agarose gel in the presence of formaldehyde [Lehrach, H. et al. (1977) Biochemistry 16: 4743–4751], transferred directly to nitrocellulose, and processed as described [Thomas, P. (1980) Proc. Natl. Acad. Sci. USA 77: 5201–5205]. Filters were hybridized with the purified cDNA insert of BP6.1 as described above (screening of cDNA library). The filters were washed twice for 20 minutes in 0.1×SSC, 0.1% SDS at 65° C. The cDNA probes were labeled as described [Thomas, P. (1980) Proc. Natl. Acad. Sci. USA 77: 5201–5205] to a specific activity of 2×10$^9$ cpm/mg.

Results

Identification and Cloning of IGFBP-5

An amino acid sequence comparison of the five known human IGFBPs revealed a high degree of homology in the NH2— and the COOH— terminal regions. The longest stretch of identical amino acids in all five of the BPs resides in two areas of the COOH— terminal region consisting of three amino acids Pro-Asn-Cys and four amino acids Cys-Trp-Cys-Val. These conserved amino acids fall within a region of the BPs that was shown to be homologous to 10 repeats within the amino terminal two thirds of the thyroglobulin molecule.

In an attempt to identify new BPs I designed degenerate primers based on these sequences and performed PCR using human osteosarcoma cDNA as a template. DNA sequence analysis of the eight PCR products yielded one sequence identical to BP2, three identical to BP4, three identical to BP5 and one unique sequence, which I designated IGFBP-5, which showed a 60% DNA sequence identity and a 76% amino acid identity to BP3.

Based on the PCR DNA sequence of IGFBP-5, I synthesized two unique IGFBP-5 DNA probes and used them to screen a λZAPII/human osteosarcoma cDNA library. From the 300,000 recombinant clones screened, I identified twelve clones which hybridized to both probes. Five clones were further purified and the cDNA inserts were analyzed by BglII and EcoRI restriction enzyme digestion and agarose gel electrophoresis. The cDNAs fell into two size classes of approximately 1.7 kb and 6 kb, which are exemplified by clones 1 and 12, respectively.

Expression of IGFBP-S mRNA

Northern blot analysis of several different tissues using 32P-labeled clone 1 cDNA, confirmed that these two size classes IGFBP-5 mRNA existed and suggested that osteoblasts are the main source of IGFBP-5 mRNA. All of the tissues tested (liver, kidney, and brain) produced IGFBP-5 mRNA but at lower levels.

Sequence Analysis of IGFBP-S

IGFBP-5 clone 1 (BP6.1) cDNA was sequenced and is shown in FIG. 1 with the deduced amino acid sequence. The amino terminal region of IGFBP-5 is hydrophobic and is presumably a signal peptide. The predicted signal peptidase cleavage (4 a) [von Heyne (1986) Nucleic Acids Research 11: 4683–4690] follows amino acid 15, yielding a nature molecule of 257 amino acids with a MW of 29,018 Da. There are no N-glycosylation sites. There are 18 cysteine residues in IGFBP-5 of which coincide with cysteine residues in BPs 1–5. There is some degree of amino acid homology between IGFBP-5 and the other five BPs, which is most pronounced in the amino and the carboxyl terminal regions of the molecules.

4. Deposit of Biological Material

Escherichia coli strain HB101 host cells transformed with pBsBP6.1 have been deposited on Dec. 18, 1990, with the American Type Culture Collection (ATCC), Rockville, Md., and given accession number 68496. This deposit will be maintained under the terms of the Budapest Treaty on the International Recognition of the Deposit of Microorganisms for purposes of patent procedure. The accession number is available from the ATCC.

This deposit is provided merely as convenience to those of skill in the art, and are not an admission that a deposit is required under 35 U.S.C. 112. The nucleic acid sequence of this plasmid, as well as the amino acid sequence of the polypeptide encoded thereby, are incorporated herein by reference and are controlling in the event of any conflict with the description herein. A license may be required to make, use, or sell the deposited material, and no such license is hereby granted.

All patents, patent applications, and references cited herein are incorporated by reference.

What is claimed is:

1. A method of treating a physiological disorder in a patient, wherein the physiological disorder results from an excessive production of free IGF comprising:

administering to the patient a therapeutically effective amount of a polypeptide capable of binding to an insulin-like growth factor selected from the group consisting of human insulin-like growth factor I and human insulin-like growth factor II, said polypeptide selected from the group consisting of (a) a polypeptide comprising an amino acid sequence that has at least 80% sequence identity to the amino acid sequence depicted at positions 1–272, of SEQ ID NO:8; (b) a polypeptide comprising an amino acid sequence that has at least 80% sequence identity to the amino acid sequence depicted at positions 16–272, of SEQ ID NO:8; (c) a polypeptide comprising an amino acid sequence that has at least 80% sequence identity to the amino acid sequence depicted at positions 21–272, of SEQ ID NO:8; and (d) a polypeptide comprising a fragment of the amino acid sequence depicted at positions 1–272 of SEQ ID NO:8 wherein said fragment comprises at least 10 consecutive amino acids thereof.

2. The method of claim 1, wherein the polypeptide comprises the amino acid sequence depicted at positions 1–272 of SEQ ID NO:8.

3. The method of claim 1, wherein the polypeptide comprises a fragment of the amino acid sequence depicted at positions 1–272 of SEQ ID NO:8 and wherein said fragment comprises at least 25 consecutive amino acids thereof.

4. The method of claim 1, wherein the polypeptide comprises the amino acid sequence depicted at positions 21–272 of SEQ ID NO:8.

5. The method of claim 1, wherein the polypeptide comprises an amino acid sequence that has at least 80% sequence identity to the amino acid sequence depicted at positions 1–272 of SEQ ID NO:8.

6. The method of claim 1, wherein the polypeptide consists of an amino acid sequence that has at least 80% sequence identity to the amino acid sequence depicted at positions 1–272 of SEQ ID NO:8.

7. The method of claim 1, wherein the polypeptide consists of an amino acid sequence that has at least 90% sequence identity to the amino acid sequence depicted at positions 1–272 of SEQ ID NO:8.

8. The method of claim 1, wherein the polypeptide consists of an amino acid sequence that has at least 95% sequence identity to the amino acid sequence depicted at positions 1–272 of SEQ ID NO:8.

9. The method of claim 1, wherein the polypeptide consists of the amino acid sequence depicted at positions 1–272 of SEQ ID NO:8.

10. The method of claim 1, wherein the polypeptide comprises an amino acid sequence that has at least 80% sequence identity to the amino acid sequence depicted at positions 16–272 of SEQ ID NO:8.

11. The method of claim 1, wherein the polypeptide consists of an amino acid sequence that has at least 80% sequence identity to the amino acid sequence depicted at positions 16–272 of SEQ ID NO:8.

12. The method of claim 1, wherein the polypeptide consists of an amino acid sequence that has at least 90% sequence identity to the amino acid sequence depicted at positions 16–272 of SEQ ID NO:8.

13. The method of claim 1, wherein the polypeptide consists of an amino acid sequence that has at least 95% sequence identity to the amino acid sequence depicted at positions 16–272 of SEQ ID NO:8.

14. The method of claim 1, wherein the polypeptide consists of the amino acid sequence depicted at positions 16–272 of SEQ ID NO:8.

15. The method of claim 1, wherein the polypeptide comprises an amino acid sequence that has at least 80% sequence identity to the amino acid sequence depicted at positions 21–272 of SEQ ID NO:8.

16. The method of claim 1, wherein the polypeptide consists of an amino acid sequence that has at least 80% sequence identity to the amino acid sequence depicted at positions 21–272 of SEQ ID NO:8.

17. The method of claim 1, wherein the polypeptide consists of an amino acid sequence that has at least 90% sequence identity to the amino acid sequence depicted at positions 21–272 of SEQ ID NO:8.

18. The method of claim 1, wherein the polypeptide consists of an amino acid sequence that has at least 95% sequence identity to the amino acid sequence depicted at positions 21–272 of SEQ ID NO:8.

19. The method of claim 1, wherein the polypeptide consists of the amino acid sequence depicted at positions 21–272 of SEQ ID NO: 8.

* * * * *

```
                        SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO: 1:

CCTGTAGATC TCCG                                                           14

(2) INFORMATION FOR SEQ ID NO: 2:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO: 2:

AATTCGGAGA TCTACAGG                                                       18

(2) INFORMATION FOR SEQ ID NO: 3:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO: 3:

AGATCTGAAT TCGCCAATGA                                                     20

(2) INFORMATION FOR SEQ ID NO: 4:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO: 4:

AGATCTAAGC TTCACCACCA CA                                                  22
```

(2) INFORMATION FOR SEQ ID NO: 5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 5:

```
GCAAAGGATT CTACAAGAG                                              19
```

(2) INFORMATION FOR SEQ ID NO: 6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 6:

```
CAAACCTTCC CGTGGCCGC                                              19
```

(2) INFORMATION FOR SEQ ID NO: 7:

(i) SEQUENCE CHARACTERISTICS:
        (A) LENGTH: 1612 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
CTCTCCTGCC CCACCCCGAG GTAAAGGGGG CGACTAAGAG AAGATGGTGT TGCTCACCGC    60
GGTCCTCCTG CTGCTGGCCG CCTATGCGGG GCCGGCCCAG AGCCTGGGCT CCTTCGTGCA   120
CTGCGAGCCC TGCGACGAGA AAGCCCTCTC CATGTGCCCC CCCAGCCCCC TGGGCTGCGA   180
GCTGGTCAAG GAGCCGGGCT GCGGCTGCTG CATGACCTGC GCCCTGGCCG AGGGGCAGTC   240
GTGCGGCGTC TACACCGAGC GCTGCGCCCA GGGGCTGCGC TGCCTCCCCC GGCAGGACGA   300
GGAGAAGCCG CTGCACGCCC TGCTGCACGG CCGCGGGGTT TGCCTCAACG AAAAGAGCTA   360
CCGCGAGCAA GTCAAGATCG AGAGAGACTC CCGTGAGCAC GAGGAGCCCA CCACCTCTGA   420
GATGGCCGAG GAGACCTACT CCCCCAAGAT CTTCCGGCCC AAACACACCC GCATCTCCGA   480
GCTGAAGGCT GAAGCAGTGA AGAAGGACCG CAGAAAGAAG CTGACCCAGT CCAAGTTTGT   540
CGGGGGAGCC GAGAACACTG CCCACCCCCG GATCATCTCT GCACCTGAGA TGAGACAGGA   600
GTCTGAGCAG GGCCCCTGCC GCAGACACAT GGAGGCTTCC CTGCAGGAGC TCAAAGCCAG   660
CCCACGCATG GTGCCCCGTG CTGTGTACCT GCCCAATTGT GACCGCAAAG GATTCTACAA   720
GAGAAAGCAG TGCAAACCTT CCCGTGGCCG CAAGCGTGGC ATCTGCTGGT GCGTGGACAA   780
GTACGGGATG AAGCTGCCAG GCATGGAGTA CGTTGACGGG GACTTTCAGT GCCACACCTT   840
CGACAGCAGC AACGTTGAGT GATGCGTCCC CCCCCAACCT TTCCCTCACC CCCTCCCACC   900
CCCAGCCCCG ACTCCAGCCA GCGCCTCCCT CCACCCCAGG ACGCCACTCA TTTCATCTCA   960
TTTAAGGGAA AAATATATAT CTATCTATTT GAGGAAACTG AGGACCTCGG AATCTCTAGC  1020
```

```
AAGGGCTCAA CTTCGAAAAT GGCAACAACA GAGATGCAAA AAGCTAAAAA GACACCCCCC      1080

CCCTTTAAAT GGTTTTCTTT TTGAGGCAAG TTGGATGAAC AGAGAAGGGA AGAGAGGAAG      1140

AACGAGAGGA AGAAGGGA AGGAAGTGTT TGTGTAGAAG AGAGAAAG ACGAATAGAG         1200

TTAGGAAAAG GAAGACAAGC AGGTGGGCAG GAAGGACATG CACCGAGACC AGGCAGGGGC      1260

CCAACTTTCA CGTCCAGCCC TGGCCTGGGG TCGGGAGAGG TGGGCGCTAG AAGATGCAGC      1320

CCAGGATGTG GCAATCAATG ACACTATTGG GGTTTCCCAG GATGGATTGG TCAGGGGAG      1380

AAAGGAAAAG GCAAAACACT CCAGGACCTC TCCCGGATCT GTCTCCTCCT CTAGCCAGCA      1440

GTATGGACAG CTGGACCCCT GAACTTCCTC TCCTCTTACC TGGGCAGAGT GTTGTCTCTC      1500

CCCAAATTTA TAAAAACTAA AATGCATTCC ATTCCTCTGA AAGCAAAACA AATTCATAAT      1560

TGAGTGATAT TAAATAGAGA GGTTTTCGGA AGCAGATCTG TGAATATGAA AT             1612
```

(2) INFORMATION FOR SEQ ID NO: 8:

(i) SEQUENCE CHARACTERISTICS:
        (A) LENGTH: 272 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

```
Met Val Leu Leu Thr Ala Val Leu Leu Leu Ala Ala Tyr Ala Gly
1               5                   10                  15

Pro Ala Gln Ser Leu Gly Ser Phe Val His Cys Glu Pro Cys Asp Glu
            20                  25                  30

Lys Ala Leu Ser Met Cys Pro Pro Ser Pro Leu Gly Cys Glu Leu Val
        35                  40                  45

Lys Glu Pro Gly Cys Gly Cys Cys Met Thr Cys Ala Leu Ala Glu Gly
    50                  55                  60

Gln Ser Cys Gly Val Tyr Thr Glu Arg Cys Ala Gln Gly Leu Arg Cys
65                  70                  75                  80

Leu Pro Arg Gln Asp Glu Glu Lys Pro Leu His Ala Leu Leu His Gly
                85                  90                  95

Arg Gly Val Cys Leu Asn Glu Lys Ser Tyr Arg Glu Gln Val Lys Ile
            100                 105                 110

Glu Arg Asp Ser Arg Glu His Glu Glu Pro Thr Thr Ser Glu Met Ala
        115                 120                 125

Glu Glu Thr Tyr Ser Pro Lys Ile Phe Arg Pro Lys His Thr Arg Ile
    130                 135                 140

Ser Glu Leu Lys Ala Glu Ala Val Lys Lys Asp Arg Arg Lys Lys Leu
145                 150                 155                 160

Thr Gln Ser Lys Phe Val Gly Gly Ala Glu Asn Thr Ala His Pro Arg
                165                 170                 175

Ile Ile Ser Ala Pro Glu Met Arg Gln Glu Ser Glu Gln Gly Pro Cys
            180                 185                 190

Arg Arg His Met Glu Ala Ser Leu Gln Glu Leu Lys Ala Ser Pro Arg
        195                 200                 205

Met Val Pro Arg Ala Val Tyr Leu Pro Asn Cys Asp Arg Lys Gly Phe
    210                 215                 220

Tyr Lys Arg Lys Gln Cys Lys Pro Ser Arg Gly Arg Lys Arg Gly Ile
225                 230                 235                 240
```

```
                               -continued

Cys Trp Cys Val Asp Lys Tyr Gly Met Lys Leu Pro Gly Met Glu Tyr
                245                 250                 255

Val Asp Gly Asp Phe Gln Cys His Thr Phe Asp Ser Ser Asn Val Glu
            260                 265                 270
```